US012583840B2

(12) United States Patent
Grumann et al.

(10) Patent No.: US 12,583,840 B2
(45) Date of Patent: Mar. 24, 2026

(54) METHOD FOR THE PREPARATION OF ANDROGEN RECEPTOR ANTAGONISTS AND INTERMEDIATES THEREOF

(71) Applicant: ORION CORPORATION, Espoo (FI)

(72) Inventors: Arne Grumann, Espoo (FI); Oskari Karjalainen, Espoo (FI)

(73) Assignee: ORION CORPORATION, Espoo (FI)

( * ) Notice: Subject to any disclaimer, the term of this patent is extended or adjusted under 35 U.S.C. 154(b) by 633 days.

(21) Appl. No.: 17/924,505

(22) PCT Filed: May 10, 2021

(86) PCT No.: PCT/FI2021/050343
§ 371 (c)(1),
(2) Date: Nov. 10, 2022

(87) PCT Pub. No.: WO2021/229145
PCT Pub. Date: Nov. 18, 2021

(65) Prior Publication Data

US 2023/0174517 A1 Jun. 8, 2023

(30) Foreign Application Priority Data

May 11, 2020 (FI) .................................... 20207081

(51) Int. Cl.

| | |
|---|---|
| ***C07D 403/12*** | (2006.01) |
| ***B01J 23/44*** | (2006.01) |
| ***B01J 27/24*** | (2006.01) |
| ***C07D 405/04*** | (2006.01) |

(52) U.S. Cl.
CPC ........... *C07D 403/12* (2013.01); *B01J 23/44* (2013.01); *B01J 27/24* (2013.01); *C07D 405/04* (2013.01)

(58) Field of Classification Search
CPC ...... C07D 403/12; C07D 405/04; B01J 23/44; B01J 27/24
See application file for complete search history.

(56) References Cited

FOREIGN PATENT DOCUMENTS

WO WO 2012/143599 A1 10/2012
WO WO 2016/162604 A1 10/2016

OTHER PUBLICATIONS

International Search Report of International Application No. PCT/FI2021/050343, mail date Jul. 27, 2021 (3 pages).
Yin et al., "Carbon-Carbon Coupling Reactions Catalyzed by Heterogeneous Palladium Catalysts," *Chemical Reviews*, vol. 107, 2007, pp. 133-173.

*Primary Examiner* — Alicia L Otton
(74) *Attorney, Agent, or Firm* — Finnegan, Henderson, Farabow, Garrett & Dunner, LLP

(57) ABSTRACT

The present invention relates to an improved process for the preparation of 2-chloro-4-(1-tetrahydro-2H-pyran-2-yl)-1H-pyrazol-5-yl)benzonitrile (III) which is useful as an intermediate in preparation of carboxamide structured androgen receptor antagonists. The process comprises preparation of compound (III) using heterogeneous palladium catalyst.

21 Claims, No Drawings

METHOD FOR THE PREPARATION OF ANDROGEN RECEPTOR ANTAGONISTS AND INTERMEDIATES THEREOF

This is a National Stage Application under 35 U.S.C. § 371 of International Patent Application No. PCT/FI2021/050343, filed May 10, 2021, which claims the benefit of priority of Finnish Patent Application No. 20207081, filed May 11, 2020, both of which are incorporated herein by reference.

TECHNICAL FIELD

The present invention relates to an improved process for the preparation of 2-chloro-4-(1-(tetrahydro-2H-pyran-2-yl)-1H-pyrazol-5-yl)benzonitrile (III) which is useful as an intermediate in the preparation of carboxamide structured androgen receptor antagonists such as N—((S)-1-(3-(3-chloro-4-cyanophenyl)-1H-pyrazol-1-yl)-propan-2-yl)-5-(1-hydroxyethyl)-1H-pyrazole-3-carboxamide (1A).

BACKGROUND OF THE INVENTION

The compound N—((S)-1-(3-(3-chloro-4-cyanophenyl)-1H-pyrazol-1-yl)-propan-2-yl)-5-(1-hydroxyethyl)-1H-pyrazole-3-carboxamide of formula (1A) and derivatives thereof have been disclosed in WO 2011/051540. Compound of formula (1A) and its derivatives are potent androgen receptor (AR) antagonists that are useful in the treatment of cancer, particularly prostate cancer and other diseases where AR antagonism is desired.

(1A)

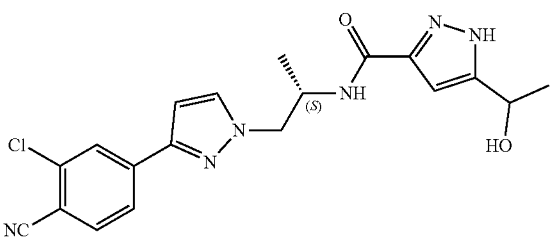

WO 2011/051540 discloses a process for the preparation of the compound of formula (1A) via intermediates of formula (III), (IV) and (V) as shown in Scheme I:

SCHEME 1

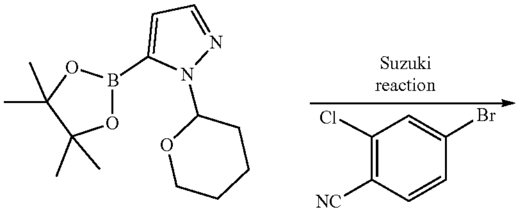

(I) (II)

-continued

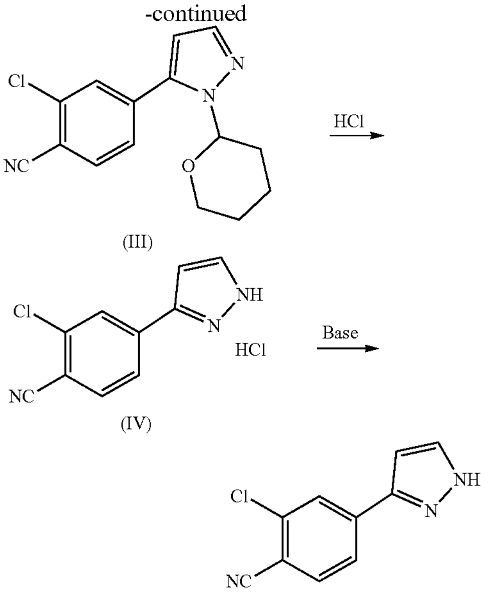

(III) (IV) (V)

The compound of formula (III) or 2-chloro-4-(1-(tetrahydro-2H-pyran-2-yl)-1H-pyrazol-5-yl)benzonitrile was prepared by reacting 1-(tetrahydro-2H-pyran-2-yl)-1H-pyrazole-5-boronic acid pinacol ester (I) with 4-bromo-2-chlorobenzonitrile (II) in a Suzuki reaction. The Suzuki reaction is carried out in the presence of homogeneous (soluble) bis(triphenylphosphine)palladium(II) chloride catalyst and sodium carbonate base in THF-water solvent. After the reaction has completed the solvents are distilled to almost dryness and water is added to precipitate the compound of formula (III).

A similar process for preparing the compound of formula (III) is disclosed in WO 2012/143599. The Suzuki reaction is carried out in the presence of homogeneous bis(triphenylphosphine)palladium(II) chloride catalyst, sodium carbonate base and phase transfer catalyst (TBAB) in THF-toluene-water solvent. The isolation of the compound of formula (III) is carried out by adding water and distilling the isolated organic phase close to dryness followed by adding ethanol and filtering the crystalline product.

Finally, WO 2016/162604 describes a method for preparing the compound of formula (III) wherein the Suzuki reaction is carried out in the presence of homogeneous $Pd(OAc)_2$ catalyst, potassium carbonate base and triphenylphosphine in an acetonitrile-water solvent. Compound of formula (III) is isolated by removing the water phase from the reaction mixture, adding ammonia water (25%) and cooling the reaction mixture followed by addition of water and isolating the crystalline product.

The above mentioned processes have the drawback that the expensive soluble palladium catalyst is disposed after the reaction contributing a significant part to the production costs and that traces of the palladium catalyst remains in the isolated product.

Thus, there is a need for a more practical and economical process that is suitable for the manufacture of AR antagonist intermediates such as the compound of formula (III) in a large scale.

SUMMARY OF THE INVENTION

It has now been found that the compound of formula (III) can be prepared in a large scale by heterogeneous catalyst resulting in high yields, high purity of the end product and short reaction times. As the heterogeneous catalyst is immobilised or supported on solid support, it can be easily recovered and recycled thereby substantially reducing the production costs of the process. The levels of catalyst residues found in the end product are also substantially reduced.

Thus the present invention provides a method for the preparation of 2-chloro-4-(1-(tetrahydro-2H-pyran-2-yl)-1H-pyrazol-5-yl)benzonitrile of formula (III)

(III)

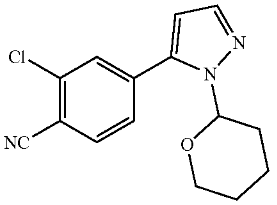

comprising reacting a compound of formula (Ia) or (Ib)

(Ia)

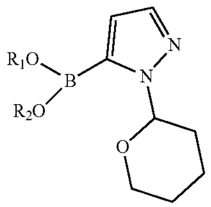

or (Ib)

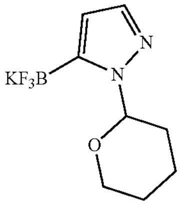

wherein $R_1$ and $R_2$ are hydrogen, or $R_1$ and $R_2$ together form a straight or a branched $C_{2-6}$ alkyl chain or a —C(O)—$CH_2$—$N(CH_3)$—$CH_2$—C(O)— chain, with 4-bromo-2-chlorobenzonitrile of formula (II)

(II)

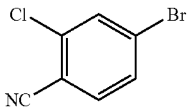

at an elevated temperature in the presence of heterogeneous palladium catalyst, a solvent and a base.

In another aspect, the present invention provides a method for the preparation of 2-chloro-4-(1H-pyrazol-3-yl)benzonitrile of formula (V)

(V)

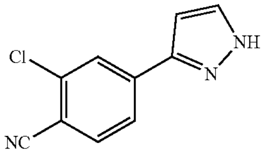

comprising the steps of (a) reacting a compound of formula (Ta) or (Ib)

(Ia)

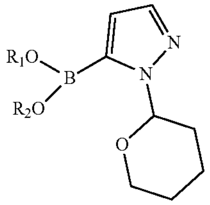

or (Ib)

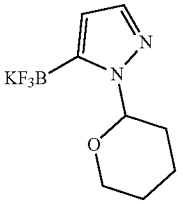

wherein $R_1$ and $R_2$ are hydrogen, or $R_1$ and $R_2$ together form a straight or a branched $C_{2-6}$ alkyl chain or a —C(O)—$CH_2$—$N(CH_3)$—$CH_2$—C(O)— chain, with 4-bromo-2-chlorobenzonitrile of formula (II)

(II)

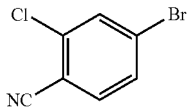

at an elevated temperature in the presence of heterogeneous palladium catalyst, a solvent and a base to obtain a compound of formula (III)

(III)

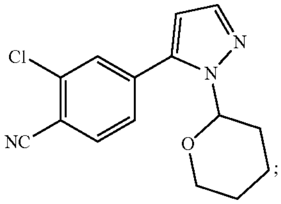

;

(b) treating the compound of formula (III) with HCl;

(c) adding a base to obtain the compound of formula (V).

In still another aspect, the present invention provides a process for the preparation of the compound of formula (1A)

(1A)

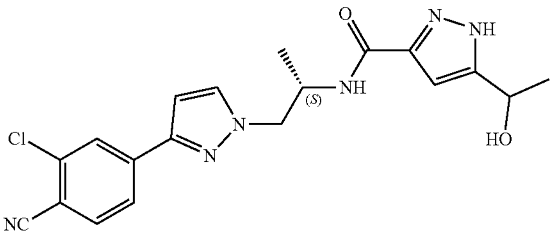

comprising the steps of (a) reacting a compound of formula (Ta) or (Ib)

(Ia)

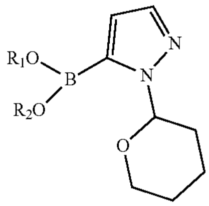

or (Ib)

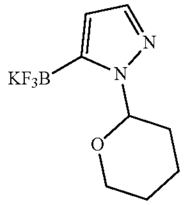

wherein $R_1$ and $R_2$ are hydrogen, or $R_1$ and $R_2$ together form a straight or a branched $C_{2-6}$ alkyl chain or a $—C(O)—CH_2—N(CH_3)—CH_2—C(O)—$ chain, with 4-bromo-2-chlorobenzonitrile of formula (II)

(II)

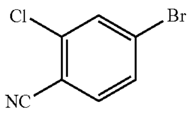

at an elevated temperature in the presence of heterogeneous palladium catalyst, a solvent and a base to obtain a compound of formula (III)

(III)

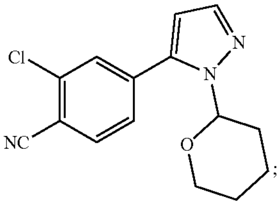

;

(b) treating the compound of formula (III) with HCl;

(c) adding a base to obtain the compound of formula (V)

(V)

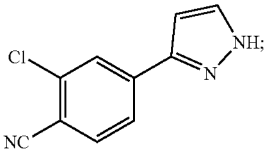

;

(d) reacting a compound of formula (V) with a compound of formula (VI)

(VI)

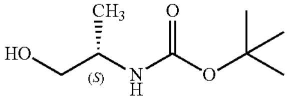

to produce a compound of formula (VII);

(VII)

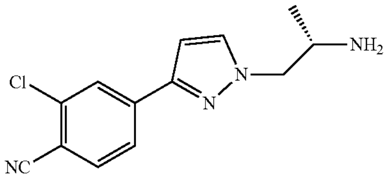

(e) reacting the compound of formula (VII) with a compound of formula (VIII)

(VIII)

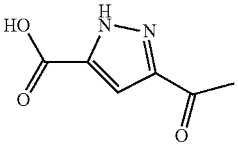

to produce a compound of formula (IX); and (IX)

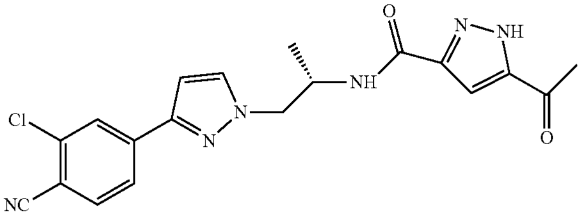

(f) reducing the compound of formula (IX) to produce the compound of formula (1A).

DETAILED DESCRIPTION OF THE INVENTION

The term "heterogeneous palladium catalyst", as used herein, refers to palladium catalyst which is immobilized or supported on solid support such that the catalyst can be readily removed from the reaction medium after completion of the reaction, for example by filtering.

The term "mol-% of palladium", as used herein, refers to the percentage of the amount of palladium (in moles) used in the reaction step in relation to the amount of starting compound (in moles). For example, if 0.005 mol of palladium is used per 1 mol of bromo-2-chlorobenzonitrile in the reaction, the mol-% of palladium used is (0.005/1)*100 mol-%=0.5 mol-%.

Tautomerism: As the hydrogen atom of the pyrazole ring may exist in tautomeric equilibrium between the 1- and 2-position, it is recognized by the skilled person that the formulas and chemical names disclosed herein comprising a hydrogen atom in the pyrazole ring are inclusive of the tautomer of the compound in question. For example, the chemical name as "2-chloro-4-(1H-pyrazol-3-yl)benzonitrile" and the corresponding formula (V) is inclusive of the tautomer of the compound, namely "2-chloro-4-(1H-pyrazol-5-yl)benzonitrile".

In accordance with the present invention, 2-chloro-4-(1-(tetrahydro-2H-pyran-2-yl)-1H-pyrazol-5-yl)benzonitrile of formula (III)

(III)

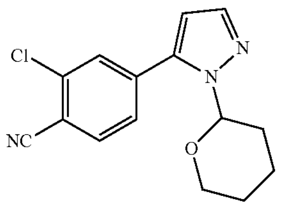

is prepared by reacting a compound of formula (Ta) or (Ib)

(Ia)

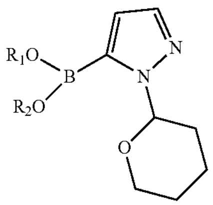

or (Ib)

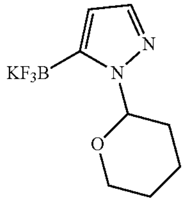

wherein $R_1$ and $R_2$ are hydrogen, or $R_1$ and $R_2$ together form a straight or a branched $C_{2-6}$ alkyl chain or a $-C(O)-CH_2-N(CH_3)-CH_2-C(O)-$ chain, with 4-bromo-2-chlorobenzonitrile of formula (II)

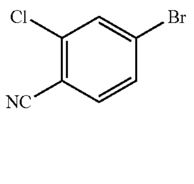

at an elevated temperature in the presence of heterogeneous palladium catalyst, a solvent and a base.

According to one preferred embodiment of the invention, the compound of formula (Ia) is selected from the following compounds:

(1)

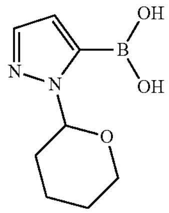

(2)

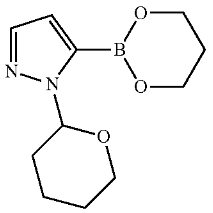

(3)

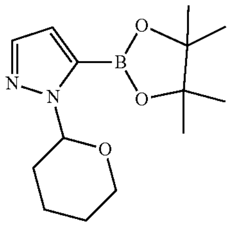

(4)

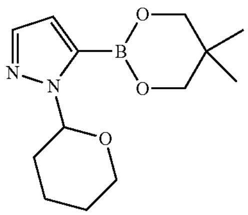

(5)

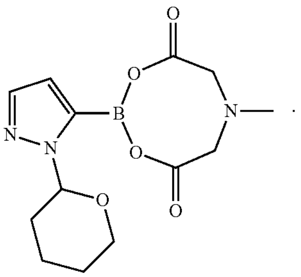

According to a particularly preferred embodiment of the invention, 4-bromo-2-chlorobenzonitrile of formula (II) is reacted with the compound of formula (Ia) which is 1-(tetrahydro-2H-pyran-2-yl)-5-(4,4,5,5-tetramethyl-1,3,2-dioxaborolan-2-yl)-1H-pyrazole (3).

The heterogeneous palladium catalyst used in the reaction is a palladium catalyst which is immobilized or supported on solid support. Examples of heterogeneous palladium catalysts include palladium on carbon, palladium on barium sulfate, palladium on metal oxides (such as alumina), palladium on silicon dioxide or palladium on zeolites. Heterogeneous palladium catalysts are commercially available, for example under trademark Noblyst® from Evonik Industries AG. Examples include Noblyst® P1064 (5% palladium on activated carbon), Noblyst® P1070 (10% palladium on activated carbon), Noblyst® P1090 (5% palladium on activated carbon), Noblyst® P1092 (5% palladium on activated carbon), Noblyst® P1093 (5% palladium on activated carbon) and Noblyst® P1095 (5% palladium on activated carbon), which are available as a wet free-flowing powder. In the method of the present invention, the amount of palladium used per amount of compound of formula (II) is typically from about 0.2 to about 1 mol-%, preferably from about 0.4 to about 0.8, mol-%, for example 0.5 mol-%. The reaction is preferably conducted in the absence of palladium ligands such as triphenylphosphine since such ligands were found to disturb the reaction when heterogeneous palladium catalysis is used.

The reaction is carried out in a suitable solvent. Whereas any suitable solvent can be used, the solvent preferably comprises dimethyl sulfoxide (DMSO) alone or, more preferably, in a mixture with water. Suitably, the ratio of water to DMSO is from about 0:100 to about 50:50, preferably from about 1:99 to about 35:65, more preferably from about 5:95 to about 20:80, for example 10:90, by volume.

Particularly suitable bases for conducting the reaction are organic bases including trialkylamines such as diisopropylethylamine (DIPEA), trimethylamine (TEA) or tributylamine (TBA). Trialkylamines are preferred and diisopropylethylamine (DIPEA) in particular, which is suitably used in an amount of 1 to 2 molar equivalent, for example from 1.3 to 1.6 molar equivalent, in relation to compound (II).

The reaction is preferably carried out in the presence of phase transfer catalyst such as a quaternary ammonium salt. Tetrabutylammonium bromide and tetrabutylammonium chloride are particularly preferred.

According to one particularly preferred embodiment of the invention, the reaction is conducted in DMSO-water solvent in the presence of a base which is diisopropylethylamine (DIPEA) and a phase transfer catalyst which is tetrabutylammonium bromide or tetrabutylammonium chloride.

The compounds of formula (Ia), (Ib) and (II) are commercially available or they can be prepared according to methods known in the art.

For carrying out the Suzuki reaction, the mixture of 4-bromo-2-chlorobenzo-nitrile (II), compound of formula (Ia) or (Ib), for example, 1-(tetrahydro-2H-pyran-2-yl)-5-(4,4,5,5-tetramethyl-1,3,2-dioxaborolan-2-yl)-1H-pyrazole (3), solvent, the base and phase transfer catalyst, may be first stirred under nitrogen atmosphere. The reaction is suitably carried out under nitrogen flow. The catalyst is added and the mixture is heated to the temperature which is from about 60° C. to about 100° C., preferably from about 70° C. to about 80° C., for example from about 72° C. to about 78° C. The mixture is agitated until the reaction is complete, for example for about 1 to about 5 h, typically for about 2 to about 4 h. Thereafter, the mixture is suitably cooled to about 50-70° C. and the heterogeneous palladium catalyst is removed, for example, by filtration under nitrogen pressure. To facilitate the removal of the heterogeneous palladium catalyst, such as palladium on carbon, from the reaction mixture, ethanol may be added to the reaction mixture before filtration. It was found that particles of palladium on carbon may form very fine dispersion in DMSO hampering the complete removal of catalyst particles from the reaction mixture by filtration. Addition of ethanol was found to result in aggregation of fine catalyst particles into larger particles which are easier to remove by filtration. The ratio of DMSO:ethanol before filtering is suitable from about 10:2 to about 10:10, more typically from about 10:3 to about 10:5, for example about 10:4.

The temperature of the filtrate is then suitably adjusted to about 30-50° C. and the precipitation of compound (III) is carried out by adding water slowly to the cooled mixture. The amount of water to be added is suitably about 60-120%, for example about 65-80%, by volume of the solvent in which the reaction was conducted. The resulting suspension can then be further cooled to about 15-25° C. and stirred for a period needed to complete the precipitation of compound (III), for example for about 3 to 12 h. The precipitated product can be isolated, for example by filtering, and washed with water and dried, for example, at reduced pressure at about 40-60° C. The method typically affords compound (III) at a HPLC purity of 99.5% or higher, more typically about 99.8%.

The conversion of the compound of formula (III) to the compound of formula (V) can be carried out using the methods known in the art. For example, the compound of formula (III) dissolved in methanol can be treated with a small amount of 30% HCl (aqueous) suitably at lowered temperature, such as 0-15° C. The mixture is stirred at this temperature for a time period necessary for the tetrahydropyranyl ring detachment to occur, for example 2 h. A base, for example ammonia water (25%), is then added to the mixture at the above temperature. Thereafter, water is added gradually, for example at 10-20° C. followed by stirring for example for a period of 6 to 24 h. The compound of formula (V) can be precipitated by cooling the mixture, for example to about 0-5° C., and stirring at this temperature for a period of time sufficient to complete the precipitation, suitably from for example from about 3 to about 5 h. The precipitated product can be isolated, for example by filtering.

The compound of formula (1A) can be prepared from the compound of formula (V), for example, using the methods described in WO 2011/051540 and WO 2012/143599. For example, according to one embodiment, the process for the preparation of the compound of formula (1A) comprises the steps of (d) reacting a compound of formula (V)

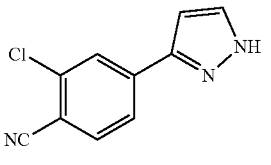

(V)

with a compound of formula (VI)

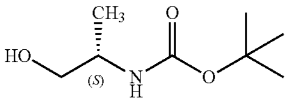

(VI)

to produce a compound of formula VII);

(VII)

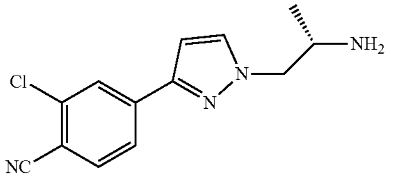

(e) reacting the compound of formula (VII) with a compound of formula (VIII)

(VIII)

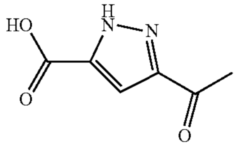

to produce a compound of formula (IX); and (IX)

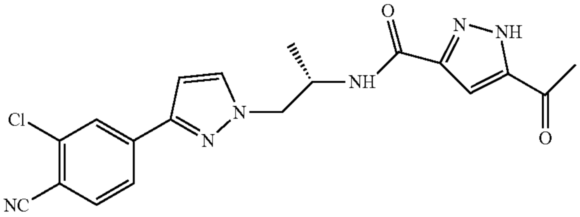

(f) reducing the compound of formula (IX) to produce the compound of formula (1A).

The reaction of step (d) can be carried out, for example, using the conditions of the Mitsunobu reaction, for example at room temperature in the presence of triphenylphosphine and DIAD (diisopropylazodicarboxylate) in a suitable solvent, for example THF or EtOAc, followed by Boc-deprotection by treatment with HCl and finally with a base such as NaOH.

The reaction step (e) can be carried out at room temperature in the presence of suitable activating and coupling agent system such as a combination of DIPEA (N,N-diisopropylethylamine), EDCI (1-ethyl-3-(3-dimethylaminopropyl) carbodiimide) and anhydrous HOBt (1-hydroxy-benzotriazole) in a suitable solvent, for example DCM. As an alternative to HOBt, HBTU (O-(benzotriazol-1-yl)-N,N,N',N'-tetramethyl-uroniumhexafluorophosphate) can be used. Alternatively, a combination of DIPEA and T3P (1-propanephosphonic acid cyclic anhydride) can be used as an activating and coupling agent system.

The reaction step (f) can be carried out at room temperature by treating the compound of formula (IX) with a reduction agent, for example sodium borohydride, in a suitable solvent, for example ethanol, followed by treating the mixture with aqueous HCl.

The invention is further illustrated by the following non-limiting examples.

Example 1. Preparation of 2-chloro-4-(1-(tetrahydro-2H-pyran-2-yl)-1H-pyrazol-5-yl)benzonitrile (III) in DMSO/Water Solvent Using Palladium on Carbon Into a flask under nitrogen was charged 4-bromo-2-chlorobenzonitrile (II) (20 g, 1 molar equivalent), 1-(tetrahydro-2H-pyran-2-yl)-5-(4,4,5,5-tetramethyl-1,3,2-dioxaborolan-2-yl)-1H-pyrazole (3) (28.4 g, 1.05 molar equivalent), tetrabutyl-ammonium bromide (1.49 g 0.05 molar equivalent), dimethyl sulfoxide (87.5 mL), water (12.5 mL) and diisopropylethylamine (24.1 mL, 1.5 molar equivalent). The mixture was degassed by evacuating using vacuum followed by reintroduction of nitrogen while vigorously stirring. The procedure was repeated three times. The catalyst (5% palladium on carbon, water wet, 1.0 g by dry weight, 0.005 molar equivalent) was added and the mixture was heated to 75° C. over 2 h. The mixture was agitated until the reaction was complete (2-3 h) after which the mixture was cooled to 65° C. Celite (2 g) and ethanol (40 mL) were added and the mixture was further agitated for about an hour. The catalyst was removed by filtration under nitrogen pressure and the filter cake was washed with dimethyl sulfoxide (10 mL). The temperature of the filtrate was adjusted to 45° C. Water (67 mL) was slowly added over about 30 minutes. The resulting suspension was cooled to 20° C. and the product was collected by filtration. The cake was washed with water (40 mL) followed by chilled ethanol (20 mL). The product was dried under vacuum at 50° C. to afford 24.5 g (92%) of the title compound (III) at 99.8 a-% purity.

Example 2. Preparation of 2-chloro-4-(1-(tetrahydro-2H-pyran-2-yl)-1H-pyrazol-5-yl)benzonitrile (III) in DMSO/Water Solvent Using Palladium on Alumina Into a flask under nitrogen was charged 4-bromo-2-chlorobenzonitrile (II) (5 g, 1 molar equivalent), 1-(tetrahydro-2H-pyran-2-yl)-5-(4,4,5,5-tetramethyl-1,3,2-dioxaborolan-2-yl)-1H-pyrazole (3) (7.1 g, 1.05 molar equivalent), tetrabutyl-ammonium bromide (0.37 g, 0.05 molar equivalent), dimethyl sulfoxide (42.5 mL), water (7.5 mL) and diisopropylethylamine (6.1 mL, 1.5 molar equivalent). The mixture was degassed by evacuating using vacuum followed by reintroduction of nitrogen while vigorously stirring. The procedure was repeated three times. The catalyst (5% palladium on alumina, 0.37 g by dry weight, 0.0075 molar equivalent) was added and the mixture was heated to 75° C. over 30 min. The mixture was agitated until the reaction was complete (2-3 h) after which the mixture was cooled to 50° C. The catalyst was removed by filtration under nitrogen pressure and the filter cake was washed with dimethyl sulfoxide (5 mL). The temperature of the filtrate was adjusted to 35° C. Water (40 mL) was slowly added over about 30 minutes. The resulting suspension was cooled to 20° C. and the product was collected by filtration. The cake was washed with water (25 mL). The product was dried under vacuum at 50° C. to afford 6.4 g (95%) of the title compound (III) at 99.8 a-% purity.

Example 3. Preparation of 2-chloro-4-(1-(tetrahydro-2H-pyran-2-yl)-1H-pyrazol-5-yl)benzonitrile (III) in DMSO/Water Solvent Using Palladium on Carbon Into a flask under nitrogen was charged 4-bromo-2-chlorobenzonitrile (II) (5 g, 1 molar equivalent), 1-(tetrahydro-2H-pyran-2-yl)-5-(4,4,5,5-tetramethyl-1,3,2-dioxaborolan-2-yl)-1H-pyrazole (3) (7.1 g, 1.05 molar equivalent), tetrabutyl-ammonium chloride (0.32 g 0.05 molar equivalent), dimethyl sulfoxide (42.5 mL), water (7.5 mL) and diisopropylethylamine (6.1 mL, 1.5 molar equivalent). The mixture was degassed by evacuating using vacuum followed by reintroduction of nitrogen while vigorously stirring. The procedure was repeated three times. The catalyst (5% palladium on carbon, water wet 0.25 g by dry weight, 0.005 molar equivalent) was added and the mixture was heated to 75° C. over 30 min. The mixture was agitated until the reaction was complete (2-3 h) after which the mixture was cooled to 50° C. The catalyst was removed by filtration under nitrogen pressure and the filter cake was washed with dimethyl sulfoxide (5 mL). The temperature of the filtrate was adjusted to 35° C. Water (40 mL) was slowly added over about 30 minutes. The resulting suspension was cooled to 20° C. and the product was collected by filtration. The cake was washed with water (25 mL). The product was dried under vacuum at 50° C. to afford 6.2 g (93%) of the title compound (III) at 99.8 a-% purity.

Example 4. Preparation of 2-chloro-4-(1-(tetrahydro-2H-pyran-2-yl)-1H-pyrazol-5-yl)benzonitrile (III) in Acetonitrile/Water Solvent Using Palladium on Carbon Into a flask under nitrogen was charged 4-bromo-2-chlorobenzonitrile (II) (5 g, 1 molar equivalent), 1-(tetrahydro-2H-pyran-2-yl)-5-(4,4,5,5-tetramethyl-1,3,2-dioxaborolan-2-yl)-1H-pyrazole (3) (7.1 g, 1.05 molar equivalent), acetonitrile (27 mL), water (18 mL) and potassium carbonate (4.5 g, 1.4 molar equivalent). The mixture was degassed by evacuating using vacuum followed by reintroduction of nitrogen while vigorously stirring. The procedure was repeated three times. The catalyst (palladium on carbon, 1.0 g by dry weight, 0.02 molar equivalent) together with triphenylphosphine (0.49 g, 0.08 eq.) were added and the mixture was heated to near reflux, about 74° C. The mixture was agitated for 2 h. At this point analysis indicated 14.4% conversion of 4-bromo-2-chlorobenzonitrile together with complete consumption of 1-(tetrahydro-2H-pyran-2-yl)-5-(4,4,5,5-tetramethyl-1,3,2-dioxa-borolan-2-yl)-1H-pyrazole (3) indicating significant decomposition of the starting compound (3).

The invention claimed is:

1. A method for the preparation of 2-chloro-4-(1-(tetrahydro-2H-pyran-2-yl)-1H-pyrazol-5-yl)benzonitrile of formula (III)

(III)

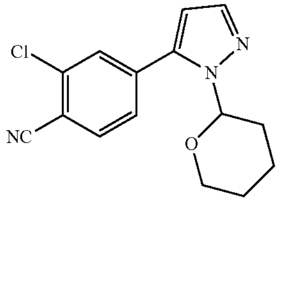

comprising reacting a compound of formula (Ia) or (Ib)

(Ia)

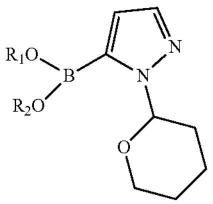

or (Ib)

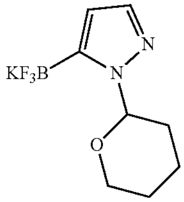

;

wherein $R_1$ and $R_2$ are hydrogen, or $R_1$ and $R_2$ together form a straight or a branched $C_{2-6}$ alkyl chain or a —C(O)—$CH_2$—$N(CH_3)$—$CH_2$—C(O)— chain, with 4-bromo-2-chlorobenzonitrile of formula (II)

(II)

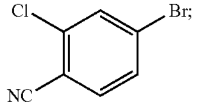

;

at an elevated temperature in the presence of a heterogeneous palladium catalyst, a solvent comprising dimethyl sulfoxide (DMSO), and a base.

2. The method according to claim 1, wherein the heterogeneous palladium catalyst is palladium on carbon, palladium on barium sulfate, palladium on metal oxides, palladium on silicon dioxide or palladium on zeolites.

3. The method according to claim 2, wherein the palladium on metal oxides is palladium on alumina.

4. The method according to claim 1, wherein the solvent comprises a mixture of dimethyl sulfoxide (DMSO) and water.

5. The method according to claim 4, wherein the ratio of water to DMSO is from about 0:100 to about 50:50.

6. The method according to claim 1, wherein the base is diisopropylethylamine (DIPEA).

7. The method according to claim 1, wherein the reaction is carried out in the presence of a phase transfer catalyst.

8. The method according to claim 7, wherein the phase transfer catalyst is a quaternary ammonium salt.

9. The method according to claim 8, wherein the quaternary ammonium salt is tetrabutylammonium bromide or tetrabutylammonium chloride.

10. The method according to claim 1, wherein the reaction is conducted in a DMSO-water solvent in the presence of a base and a phase transfer catalyst, wherein the base is diisopropylethylamine (DIPEA), and the phase transfer catalyst is tetrabutylammonium bromide or tetrabutylammonium chloride.

11. The method according to claim 1, wherein the reaction temperature is from about 60° C. to about 100° C.

12. The method according to claim 1, wherein the amount of palladium catalyst used per amount of compound of formula (II) is from about 0.2 to about 1 mol-%.

13. The method according to claim 1, wherein the reaction is carried out under nitrogen atmosphere.

14. The method according to claim 1, wherein the reaction time is 1-5 h.

15. The method according to claim 1, further comprising the steps of:

(b) removing the catalyst from the reaction mixture;

(c) adding water to the cooled reaction mixture; and d) isolating the precipitated compound of formula (III).

16. The method according to claim 15, further comprising adding ethanol to the reaction mixture before removing the catalyst from the reaction mixture.

17. The method according to claim 15, wherein the isolation of the compound of formula (III) is carried out at 10-30° C.

18. The method according to claim 1, wherein the compound of formula (Ia) is selected from the following compounds:

(1)

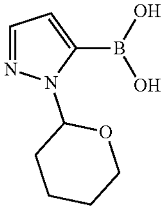

(2)

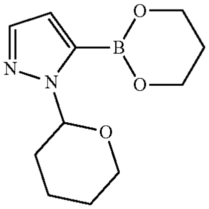

(3)

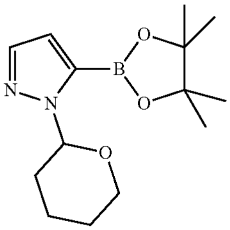

(4)

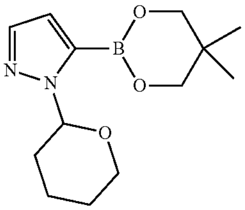

-continued (5)

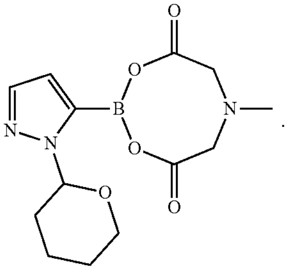

19. The method according to claim 18, wherein the compound of formula (Ia) is 1-(tetrahydro-2H-pyran-2-yl)-5-(4,4,5,5-tetramethyl-1,3,2-dioxaborolan-2-yl)-1H-pyrazole (3).

20. A method for the preparation of 2-chloro-4-(1H-pyrazol-3-yl)benzonitrile of formula (V)

(V)

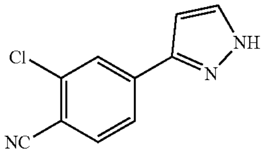

comprising the steps of:

(a) reacting a compound of formula (Ia) or (Ib)

(Ia)

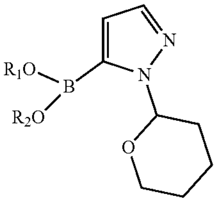

or (Ib)

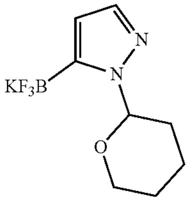

;

wherein $R_1$ and $R_2$ are hydrogen, or $R_1$ and $R_2$ together form a straight or a branched $C_{2-6}$ alkyl chain or a $-C(O)-CH_2-N(CH_3)-CH_2-C(O)-$ chain, with 4-bromo-2-chlorobenzonitrile of formula (II)

(II)

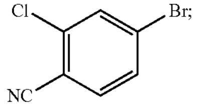

at an elevated temperature in the presence of heterogeneous palladium catalyst, a solvent comprising dimethyl sulfoxide (DMSO), and a base to obtain a compound of formula (III)

(III)

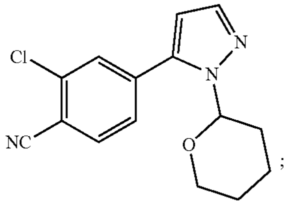

(b) treating the compound of formula (III) with HCl;

(c) adding a base to obtain the compound of formula (V).

21. A method for the preparation of the compound of formula (1A)

(1A)

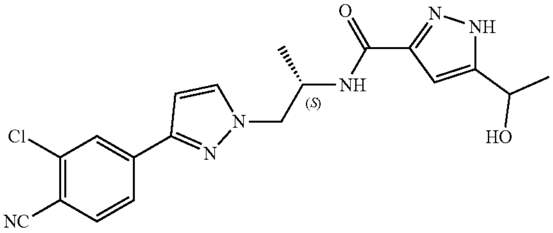

comprising the steps of:

(a) reacting a compound of formula (Ia) or (Ib)

(Ia)

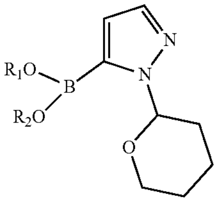

or (Ib)

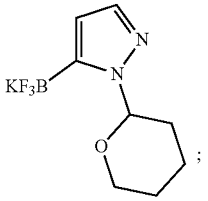

wherein $R_1$ and $R_2$ are hydrogen, or $R_1$ and $R_2$ together form a straight or a branched $C_{2-6}$ alkyl chain or a —C(O)—$CH_2$—$N(CH_3)$—$CH_2$—C(O)— chain, with 4-bromo-2-chlorobenzonitrile of formula (II)

(II)

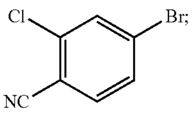

at an elevated temperature in the presence of a heterogeneous palladium catalyst, a solvent comprising dimethyl sulfoxide (DMSO), and a base to obtain a compound of formula (III)

(III)

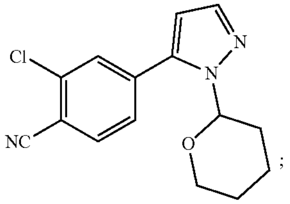

(b) treating the compound of formula (III) with HCl;

(c) adding a base to obtain the compound of formula (V)

(V)

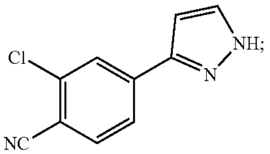

(d) reacting a compound of formula (V) with a compound of formula (VI)

(VI)

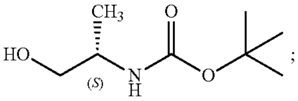

to produce a compound of formula (VII)

(VII)

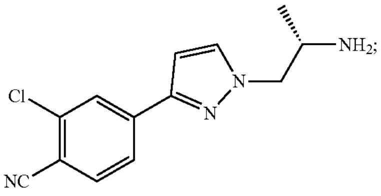

(e) reacting the compound of formula (VII) with a compound of formula (VIII)

(VIII)

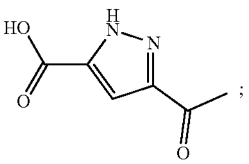

to produce a compound of formula (IX)
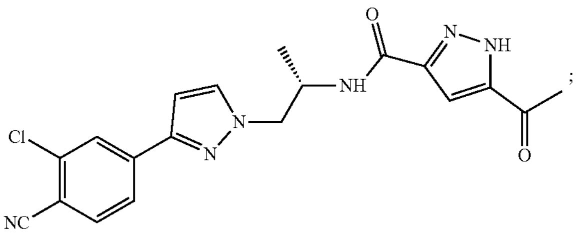
(IX)
and
(f) reducing the compound of formula (IX) to produce the compound of formula (1A).
* * * * *